United States Patent
Haught et al.

(10) Patent No.: US 8,609,070 B2
(45) Date of Patent: Dec. 17, 2013

(54) PROCESS FOR MAKING IMPROVED ORAL COMPOSITIONS

(75) Inventors: John Christian Haught, West Chester, OH (US); Marc Alan Hester, Cincinnati, OH (US); Steven Hamilton Hoke, II, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 57 days.

(21) Appl. No.: 13/105,181

(22) Filed: May 11, 2011

(65) Prior Publication Data

US 2011/0280814 A1 Nov. 17, 2011

Related U.S. Application Data

(60) Provisional application No. 61/333,577, filed on May 11, 2010.

(51) Int. Cl.
| | | |
|---|---|---|
| *A61K 8/44* | (2006.01) | |
| *A61Q 11/00* | (2006.01) | |
| *A61K 8/49* | (2006.01) | |
| *A61K 8/55* | (2006.01) | |
| *A61K 8/46* | (2006.01) | |

(52) U.S. Cl.
USPC .......................................... 424/49; 426/486

(58) Field of Classification Search
USPC .......................................... 424/49; 556/105
See application file for complete search history.

(56) References Cited

FOREIGN PATENT DOCUMENTS

| CN | 101 602 776 | 12/2009 |
|---|---|---|
| DE | 11 36 711 | 9/1962 |
| JP | 2004107270 * | 4/2004 |
| WO | WO 03/068181 A1 | 8/2003 |
| WO | WO 2005/002598 A1 | 1/2005 |

OTHER PUBLICATIONS

MeadWestvaco, Carbon Department "Nuchar HD", Product Data Bulletin, Dec. 2007.*
International Search Report PCT/US2011/036077, dated Oct. 10, 2011.

* cited by examiner

*Primary Examiner* — Walter Webb
(74) *Attorney, Agent, or Firm* — Armina E. Stricklin

(57) ABSTRACT

Processes for preparing an oral care composition having improved taste, color, odor and/or clarity, wherein said processes comprise the steps of: providing an unfiltered dentifrice component selected from unfiltered alkyl phosphate surfactants, alkyl phosphate ethoxylated surfactants, lauryl sulfate surfactants, betaine surfactants, antibacterial agents, cetyl pyridinium chloride, metal Salts, phytic acids, or mixtures thereof; filtering the unfiltered dentifrice component with an adsorbent to form a filtered dentifrice component; and incorporating the filtered dentifrice component into the oral care composition. In one such process, activated carbon with a median particle size of less than or equal to about 30 μm, optionally a macro-mesoporous:microporous ratio about 0.9 or higher and optionally a BET per Total Volume of equal to or less than about 1600 m^2/g, has been found to remove undesirable contaminants from oral care dentifrice components, such as alkyl phosphate surfactant, alkyl phosphate ethoxylated surfactant, lauryl sulfate surfactant, betaine surfactants, antibacterial agents, cetyl pyridinium chloride, metal salts, or phytic acid.

18 Claims, No Drawings

PROCESS FOR MAKING IMPROVED ORAL COMPOSITIONS

CROSS REFERENCE TO RELATED APPLICATION

This application claims the benefit of U.S. Provisional Application No. 61/333,577, filed May 11, 2010, which is incorporated herein by reference.

FIELD OF THE INVENTION

The present invention relates to oral compositions containing oral care components with undesirable by-products or contaminants and improved process for making oral compositions.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual efficacy. Since many efficacious oral care components have undesirable taste, color, odor or clarity, efforts to improve these characteristics are common in the art. For taste, one way to remedy an undesirable product taste is to add additional components, such as flavors, that will improve the overall taste experience for the consumer. However, such remedies can be expensive and it may be difficult to entirely mask an undesirable taste. Improvement of color or clarity through dyes or other additives has similar issues.

Activated carbons are generally known in the art as useful for filtering/purifying water (due to their adsorbent behavior and large surface area) by removing undesirable constituents, such as chlorine, sediment, organics, viruses, and volatile organic compounds. They have also been utilized in chemical processing to reduce or eliminate undesirable by-products or contaminants. Activated carbons are known to be less effective at removing minerals, salts, and dissolved inorganic compounds.

In JP 2004107270, activated carbon was also taught to be used to remove odiferous and discoloring species from a phosphate ester surfactant.

Therefore, there is still an interest in finding ways to improve the overall taste, color, odor and/or clarity of food-grade materials such as those used in an oral care composition that are efficacious, cost-effective, and desirable to consumers.

SUMMARY OF THE INVENTION

It has now been surprisingly found that certain activated carbon materials can be used to remove undesirable by-products/contaminants found in oral care components so as to improve the overall taste, color, odor and/or clarity of a resulting oral care composition. The present invention is therefore directed to a process of using such activated carbon materials to reduce or remove undesirable tasting components, discoloration and/or microbes during or after the synthesis or prior to use in oral care compositions of unfiltered oral care components including: alkyl phosphate surfactants (with or without esterification), lauryl sulfate surfactant, betaine surfactants, antibacterial agents, cetyl pyridinium chloride, metal salts, and/or phytic acid. The process of the invention involves contacting the oral care component with an activated carbon adsorbent. The contact time is at least 30 seconds, where the adsorbent is mixed with the unfiltered oral care component and then the adsorbent is filtered out of the solution to yield a purified oral care component. Secondarily, the adsorbent can be immobilized into a cartridge or column and the unfiltered oral care component is passed over the adsorbent, where the residence time of the oral care component is at least 30 seconds. The activated carbon may be further housed in a filter with filler material to hold the carbon in place.

In one embodiment, the present invention relates to process for preparing an oral care composition having improved taste, color, odor and/or clarity, wherein said composition comprises a dentifrice component;
wherein said process comprises the steps of:
  a) providing an unfiltered dentifrice component selected from unfiltered alkyl phosphate surfactants, alkyl phosphate ethoxylated surfactants, lauryl sulfate surfactants, betaine surfactants, antibacterial agents, cetyl pyridinium chloride, metal salts, phytic acids, or mixtures thereof;
  b) filtering the unfiltered dentifrice component with an adsorbent selected from activated carbon having a mean particle size of less than 30 microns, to form a filtered dentifrice component; and
  c) incorporating the filtered dentifrice component into the oral care composition.

In another embodiment, the present invention relates to the use of an adsorbent to filter an oral care surfactant selected from alkyl phosphate surfactants, ethoxylated alkyl phosphate surfactants, and mixtures thereof to improve the taste, color, odor and/or clarity of an oral care composition comprising said oral care surfactant.

In another embodiment, the present invention relates to a method for improving taste, color, odor and/or clarity of an oral care composition, comprising:
  a) providing an unfiltered surfactant wherein the unfiltered surfactant is selected from alkyl phosphate surfactants, ethoxylated alkyl phosphate surfactants, and mixtures thereof;
  b) filtering the unfiltered surfactant with an adsorbent selected from activated carbon having a macro-mesoporous:microporous ratio of at least about 0.9, to form a filtered surfactant; and
  c) incorporating the filtered surfactant into the oral care composition.

In another embodiment, the present invention relates to a process, method and/or use above wherein the activated carbon has a macro-mesoporous:microporous ratio of at least about 9.

In another embodiment, the present invention relates to a process, method and/or use above wherein the activated carbon has a macro-mesoporous:microporous ratio of from about 0.9 to about 2.

In another embodiment, the present invention relates to a process, method and/or use above wherein the activated carbon particles are at least partially coated with an active agent to aid in adsorption.

In another embodiment, the present invention relates to a process, method and/or use above wherein the activated carbon has a BET:Total Volume of less than 1600 m^2/g.

In another embodiment, the present invention relates to a process, method and/or use above wherein the unfiltered dentifrice component is an unfiltered surfactant selected from unfiltered alkyl phosphate surfactants, unfiltered alkyl phosphate ethoxylated surfactants, unfiltered lauryl sulfate surfactants, unfiltered betaine surfactants, and mixtures thereof and the filtered dentifrice component corresponds to the filtered version of the selected unfiltered dentifrice component.

In another embodiment, the present invention relates to a process, method and/or use above wherein during the filtering step (b), the unfiltered dentifrice component is in contact with the adsorbent for at least 30 seconds.

In another embodiment, the present invention relates to a process, method and/or use above wherein during the filtering step (b), the adsorbent is mixed with the unfiltered dentifrice component to form a solution and then the adsorbent is removed from the solution to form the filtered dentifrice component.

In another embodiment, the present invention relates to a process, method and/or use above wherein during the filtering step (b), the adsorbent is immobilized into a cartridge and/or column and the unfiltered dentifrice component is then passed through the column and collected to form the filtered dentifrice component.

In another embodiment, the present invention relates to a process, method and/or use above wherein during the filtering step (b), a filter is constructed out of the adsorbent and then the unfiltered dentifrice component is then passed through the filter and collected to form the unfiltered dentifrice component.

In another embodiment, the present invention relates to a process, method and/or use above wherein the adsorbent is selected from activated carbon particles having a particle size a median particle size of less than or equal to about 25 μm.

In another embodiment, the present invention relates to a process, method and/or use above wherein the adsorbent is selected from activated carbon particles having a particle span from about 4 or less.

In another embodiment, the present invention relates to a process, method and/or use above wherein the unfiltered dentifrice component is passed through the filter at a flow rate of from about 0.001 liters/min to about 100 liters/min.

In another embodiment, the present invention relates to a process, method and/or use above wherein the filtered dentifrice component is then recirculated through the adsorbent until the desired amount of contaminant is removed.

In another embodiment, the present invention relates to a process, method and/or use above wherein multiple adsorbents are connected in series.

In another embodiment, the present invention relates to a process, method and/or use above wherein multiple adsorbents are packed in zones within the column and/or cartridge.

In another embodiment, the present invention relates to a process, method and/or use above wherein the activated carbon has a mean particle size of less than 30 microns and a particle span of 4.0 or less.

DETAILED DESCRIPTION OF THE INVENTION

The present invention relates to a process for preparing an oral care composition having improved taste, color, odor and/or clarity, wherein said composition comprises a dentifrice component and wherein said process comprises the steps of: providing an unfiltered dentifrice component selected from unfiltered alkyl phosphate surfactants, alkyl phosphate ethoxylated surfactants, lauryl sulfate surfactants, betaine surfactants, antibacterial agents, cetyl pyridinium chloride, metal salts, phytic acids, or mixtures thereof; filtering the unfiltered dentifrice component with an adsorbent, selected from activated carbon having a macro-mesoporous:microporous ratio of at least about 0.9, to form a filtered dentifrice component; and incorporating the filtered dentifrice component into the oral care composition. These elements will be discussed in more detail below.

Oral Care Composition

As used herein, "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

Dentifrice Component

As used herein, "dentifrice component" refers generally to both filtered and unfiltered versions of materials selected from alkyl phosphate surfactants, alkyl phosphate ethoxylated surfactants, lauryl sulfate surfactants, betaine surfactants, antibacterial agents, cetyl pyridinium chloride, metal salts, phytic acids, or mixtures thereof. Without being limited by theory, Applicants recognize that "filtered" is a matter of degree and therefore "filtered" and "unfiltered" are used in a relational sense to describe a (what is often a "raw") material that has greater or fewer impurities, by-products and/or contaminants than another. Therefore, a filtered dentifrice component is one that was provided in relatively unfiltered form but then has been treated in order to remove at least some measurable amount of impurities, by-products and/or contaminants.

As used herein, the term "contaminants" refers to species that cause a soapy taste, stinky odor, or otherwise unpleasant properties, such as amines, amides, organoamines, sulfides, sulfates, sulfites, organosulfur species, aminosulfur species, unsaturated hydrocarbons, fatty alcohols, fatty acids, amino acids, metals, phenolics, aryl halides, ethoxylated hydrocarbons, ethoxylated fatty alcohols, pyrazines, lactones, ringed hydrocarbons, ethers, esters, and tetrahydrofurans.

In one embodiment, the unfiltered dentifrice component is selected from unfiltered alkyl phosphate surfactants, unfiltered alkyl phosphate ethoxylated surfactants, unfiltered lauryl sulfate surfactants, unfiltered betaine surfactants, and mixtures thereof and the filtered dentifrice component corresponds to the filtered version of the selected unfiltered dentifrice component but-for the absence of measurable amounts of impurities, by-products and/or contaminants.

In one embodiment, the unfiltered dentifrice components useful herein include off-tasting components as a result of impurities, by-products and/or contaminants. Such off-tasting components may be described by consumers as soapy, bitter, metallic, earthy or dirty, and astringent. Soapy is typically characterized by the presence of dodecanal or dodecanol. Bitter is typically characterized by the presence of quinine. Earthy and dirty are typically characterized by a soil like taste or odor, such as mushrooms. Metallic is typically characterized by the presence of zinc and its salts that leave a 'metal' taste in the mouth.

In one embodiment, the dentifrice components herein are selected from surfactants including anionic alkyl phosphates.

Alkyl Phosphates

The anionic surfactants useful herein as dentifrice components are alkyl phosphates. The surface active organophosphate agents have a strong affinity for enamel surface and have sufficient surface binding propensity to desorb pellicle proteins and remain affixed to enamel surfaces. Suitable examples of organophosphate compounds include mono-, dior triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

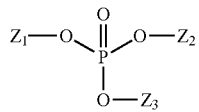

Some other agents include alkyl or alkenyl phosphate esters represented by the following structure:

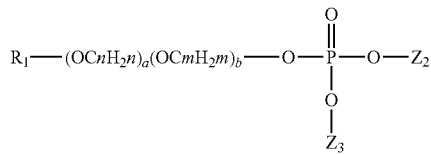

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b- group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocamidopropyl betaine (CAPB), and lauramidopropyl betaine. The unwanted tastes often associated with these surfactants are soapy, chemical, and/or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The unwanted tastes often associated with these surfactants are soapy, chemical, and/or artificial.

Filtering with an Adsorbent

The processes of the present invention include a step of filtering the unfiltered dentifrice component with an adsorbent to form a filtered dentifrice component.

Adsorbent

As used herein, "adsorbent" refers to any substance that has the ability to condense or hold molecules of other substances on its surface. Surprisingly, activated carbon particles having a selected particle size distribution and optionally selected ratio of macro-mesoporous to microporous pore volumes have been found (without being limited by theory) to be useful in filtering dentifrice components.

In one embodiment, the activated carbon adsorbent is selected from activated carbon powders, activated carbon granules, and mixtures thereof.

In one embodiment the adsorbent is selected from activated carbon which may be at least partially coated with an active agent to aid in adsorption. As used herein, the term "activated carbon particles" or "activated carbon filter particles" and their derivatives are intended to refer to carbon particles that have been subjected to an activation process. As used herein, the term "activation" and its derivatives are intended to refer to a process in which a carbonized substance is rendered more porous.

In one embodiment, the adsorbent comprises activated carbon particles having a median particle size of less than or equal to about 30 μm, alternatively less than or equal to about 25 μm, alternatively about 22 μm. In one embodiment, the activated carbon particles have a particle span from about 4 or less, alternatively from about 3 or less.

In one embodiment, the activated carbon has a macro-mesoporous:microporous ratio of at least about 0.9 or higher and may have a BET per Total Volume of equal to or less than about 100 m^2/g as exemplified in Table 1.

As used herein, the term "micropore" is intended to refer to an intra-particle pore having a width or diameter less than 2 nm (or equivalently, 20 A). As used herein, the term "mesopore" is intended to refer to an intra-particle pore having a width or diameter between 2 nm and 50 nm (or equivalently, between 20 A and 500 A). As used herein, the term "macropore" is intended to refer to an intra-particle pore having a width or diameter greater than 50 nrn (or equivalently, 500 A).

As used herein, the phrase "total pore volume" and its derivatives are intended to refer to the volume of all the intra-particle pores, i.e., micropores, mesopores, and macropores. The total pore volume is calculated as the volume of nitrogen adsorbed at a relative pressure of 0.9814 using the "BET" process (Brunauer, Emmett, and Teller process per ASTM D 4820-99 standard), a process well known in the art. As used herein, the phrase "micropore volume" and its derivatives are intended to refer to the volume of all micropores. The micropore volume is calculated from the volume of nitrogen adsorbed at a relative pressure of 0.15 using the BET process. As used herein, the phrase "sum of the mesopore and macropore volumes" and its derivatives are intended to refer to the volume of all mesopores and macropores. The sum of the mesopore and macropore volumes is equal to the difference between the total pore volume and micropore volume, or equivalently, is calculated from the difference between the volumes of nitrogen adsorbed at relative pressures of 0.9814 and 0.15 using the BET process.

As used herein, the phrase "pore size distribution in the mesopore range" is intended to refer to the distribution of the pore size as calculated by the Barrett, Joyner, and Halenda (BJH) process, a process well known in the art.

As used herein, the term "carbonization" and its derivatives are intended to refer to a process in which the non-carbon atoms in a carbonaceous substance are reduced.

As used herein, the phrase "point of zero charge" is intended to refer to the pH above which the total surface of the carbon particles is negatively charged. A test procedure used to determine this value can be found in International Application No. PCT/US03/05416, Feb. 21, 2003, and also in International Application No. PCT/US03/05409, filed Feb. 21, 2003, the substances of which are incorporated herein by reference.

As used herein, the term "basic" is intended to refer to filter particles with a point of zero charge greater than 7. As used herein, the term "acidic" is intended to refer to filter particles with a point of zero charge less than 7.

As used herein, the phrase "mesoporous activated carbon filter particle" refers to an activated carbon filter particle wherein the sum of the mesopore and macropore volumes may be greater than 0.12 mL/g. As used herein, the phrase "microporous activated carbon filter particle" refers to an activated carbon filter particle wherein the sum of the mesopore and macropore volumes may be less than 0.12 mL/g. As used herein, the phrase "mesoporous and basic activated carbon filter particle" is intended to refer to an activated carbon filter particle wherein the sum of the mesopore and macropore volumes may be greater than 0.12 mL/g and has a point of zero charge greater than 7.

As used herein, the phrase "mesoporous, basic, and reduced-oxygen activated carbon filter particle" is intended to refer to an activated carbon filter particle wherein the sum of the mesopore and macropore volumes may be greater than 0.12 mL/g, has a point of zero charge greater than 7, and has a bulk oxygen percentage by weight of 1.5% or less. As used herein, the phrase "mesoporous and acidic activated carbon filter particle" is intended to refer to an activated carbon filter particle wherein the sum of the mesopore and macropore volumes may be greater than 0.12 mL/g and has a point of zero charge less than 7.

As used herein, the phrase "starting material" refers to any precursor containing mesopores and macropores or capable of yielding mesopores and macropores during carbonization and/or activation.

Filtering

The process of the invention involves contacting the unfiltered dentifrice component with the adsorbent, the contact time is at least 30 seconds. In one embodiment, the adsorbent is mixed with the unfiltered dentifrice component to form a solution and then the adsorbent is removed from the solution to form the filtered dentifrice component. In another embodiment, the adsorbent is immobilized into a cartridge and/or column and the unfiltered dentifrice component is then passed through the column and collected to form the filtered dentifrice component.

In one embodiment, a filter may be constructed out of the adsorbent and then the unfiltered dentifrice component is passed through the filter and collected to form the unfiltered dentifrice component.

The flow rate of the unfiltered dentifrice component through the adsorbent may be from about 0.001 liters/min to about 100 liters/min.

In one embodiment, the filtered dentifrice component is recirculated through the adsorbent until the desired amount of contaminant is removed. In another embodiment, multiple adsorbents are connected in series or are packed in zones within the column and/or cartridge.

As used herein, the terms "filters" and "filtration" refer to structures and mechanisms, respectively, associated with microorganism removal (and/or other contaminant removal), via primarily adsorption and/or size exclusion to a lesser extent.

As used herein, the terms "removal", "reduce", "reduction", and their derivatives refer to partial reduction of the number or concentration of contaminants.

As used herein, the phrase "filter material" is intended to refer to an aggregate of filter particles. The aggregate of the filter particles forming a filter material can be either homogeneous or heterogeneous. The filter particles can be uniformly or non-uniformly distributed (e.g., layers of different filter particles) within the filter material. The filter particles forming a filter material also need not be identical in shape or size and may be provided in either a loose or interconnected form. For example, a filter material might comprise microporous, and mesoporous and basic activated carbon particles in combination with activated carbon fibers, and these filter particles may be either provided in loose association or partially or wholly bonded by a polymeric binder or other means to form an integral structure. Further, the filter material may be in the form of fibers or sheets.

As used herein, the phrase "filter particle" is intended to refer to an individual member or piece, which is used to form at least part of a filter material. For example, a fiber, a granule, a bead, etc. are each considered filter particles herein. Further, the filter particles can vary in size, from impalpable filter particles (e.g., a very fine powder) to palpable filter particles.

Incorporating Filtered Dentifrice Component

The processes of the present invention include a step of incorporating the filtered dentifrice component into the oral care composition. "Oral Care Composition" as used herein includes toothpaste, dentifrice, tooth gel, subgingival gel, mouthrinse, mousse, foam, mouthspray, lozenge, chewable tablet, chewing gum or denture product, The oral care composition may also be incorporated onto strips or films for direct application or attachment to oral surfaces. Traditional methods for incorporating the filtered dentifrice component into the oral care composition may be used.

Procedure for Assessing Adsorbent Efficacy:

1. Supply an unfiltered surfactant.
2. To the unfiltered surfactant, add at least 2% activated carbon from Table I.
3. Stir this surfactant plus carbon mixture for a minimum of 30 minutes to 16 hours, preferably 8 hours.
4. Then filter the surfactant through water washed vacuum filter (0.45 micron pore size, VWR catalog #28199-688).
5. Water wash the filter; pass at least 250 ml water through the filter, to remove residual PEG on the cellulose acetate and then add the surfactant and collect the retentate as purified surfactant without the carbon particles. Alternatively, a metal screen with a mesh size smaller than the carbon could be used to remove the carbon from the surfactant.
6. Collect the headspace over the treated and untreated alkyl phosphate sample (MAP 213-S) using Solid Phase Microextraction (SPME).

7. Thermally desorb the collected materials from the SPME fiber and analyze using a GC separation with both olfactometry (sniff port) and mass spectrometry detection to obtain both the odor impact and the molecular identity of individual components. For a given surfactant, compare the results from both before and after the filtering/treatment process The procedure above could be performed by fixing the carbon or adsorbent into a housing with screen to prevent particles from escaping and flowing the contaminated solution through the housing.

For in-use evaluation of the carbon efficacy, alkyl phosphate was filtered through the carbon and then formulated into an oral care composition. The oral care composition was then evaluated for soapy character and bitter aftertaste. The results of that testing showed that the filtered alkyl phosphate eliminated nearly all of the soapy character and greatly reduced the bitter off taste.

Assessing Particle Size Distribution:

As used herein, the phrase "median particle size" refers to the diameter of a particle below or above which 50% of the total volume of particles lies. This median particle size is designated as $D_{v,0.50}$.

Further, the phrase, "particle span" is a statistical representation of a given particle sample and can be calculated as follows. First, the median particle size, $D_{v,0.50}$, is calculated as described above. Then by a similar method, the particle size that separates the particle sample at the 10% by volume fraction, $D_{v,0.10}$, is determined, and then the particle size that separates the particle sample at the 90% by volume fraction, $D_{v,0.90}$, is determined. The particle span is then equal to: $(D_{v,0.90}-D_{v,0.10})/D_{v,0.50}$.

Particle size measurement is based on the principle of laser diffraction technique. Particles can range in size from very fine to coarse depending on the materials being measured. Particles pass through an optical beam that will scatter light at an angle that is directly proportional to its size. Large particles scatter light at narrow angles with high intensity. Small particles scatter light at wider angles with low intensity. Using a series of detectors it measures the light pattern produced over a wide variety of angles. The instrument then measures this energy by calculating volume size distribution by transformation of the observed diffraction pattern produced. The Mastersizer 2000 has the capability to measure particles over the range of 0.02 μm to 2000 μm using it's series of detectors. Using the Mastersizer 2000 it allows users to obtain relevant data such as sieve sizes, volume weighed mean, span, and other significant data that can be of importance to the end user.

This method details the analysis of dry powder samples using a Sirocco 2000 dry-powder dispersion unit attached to a Mastersizer 2000. The powder sample is introduced into the Sirocco 2000 via a "general purpose tray". Dispersion is achieved in two phases: when air pressure is applied to the powder sample and as the particles rapidly accelerate through the air stream. The sample feed rate is automatically controlled and depends upon the relative obscuration of the light source by the sample; for dry powders it is recommended to maintain an obscuration level of 0.2%-20%. It is recommended that the entire sample placed on the dry powder feeder tray be measured; this ensures no sample bias due to segregation during sample delivery. Samples being measured by Mastersizer must be stored properly to avoid moisture intake which may negatively affect dispersion and analysis. For the measurements reported herein, the MALVERN Mastersizer 2000 Particle Sizer (Malvern Instruments, Inc., Southborough, Mass. 01772) was used to evaluate the carbon particle sizes.

While many methods and machines are known to those skilled in the art for fractionating particles into discreet sizes, sieving is one of the easiest, least expensive and common ways to ensure particles are of a uniform size and distribution.

EXAMPLES

TABLE I

Activated Carbon Properties

| Material | BET (m^2/g) | V(micro) ml/g | Vol (meso-macro) ml/g | Total Vol ml/g | Density g/cm^3 | meso-macro/ micro | BET area/ Total Vol m^2/ml |
|---|---|---|---|---|---|---|---|
| Mallinckrodt Activated Charcoal (Organic) | 960 | 0.42 | 0.4 | 0.82 | 0.76 | 0.95 | 1170.7 |
| Activated Carbon NUCHAR HD | 1591 | 0.68 | 0.88 | 1.56 | 0.49 | 1.29 | 1019.9 |
| SA 1500 | 2139 | 0.87 | 0.56 | 1.43 | 0.52 | 0.64 | 1495.8 |
| SA 20 | 1631 | 0.65 | 0.58 | 1.23 | 0.58 | 0.89 | 1326.0 |

The activated charcoal/carbon in Table I are commercially available from Sigma Aldrich (Mallinckrodt Activated Carbon) or from Meadwestvaco (Nuchar HD, Nuchar SA1500, and Nuchar SA20).

TABLE III

Commercially Available Activated Carbon - Particle Size Distributions

| Sample Name | D (v, 0.1) | D (v, 0.5) | D (v, 0.9) |
|---|---|---|---|
| Nuchar HD - Average | 5.515 | 22.086 | 65.146 |
| Nuchar SA-1500 - Average | 6.063 | 39.541 | 102.565 |
| Nuchar SA-20 - Average | 6.445 | 30.733 | 75.194 |
| Mallinckrodt Activated Charcoal - Average | 4.018 | 24.802 | 102.871 |

D(v, 0.1) - 10% of the volume distribution is below this value
D(v, 0.5) - 50% of the volume distribution is below this value
D(v, 0.9) - 90% of the volume distribution is below this value The data from table III was determined from a MALVERN Mastersizer 2000 Particle with a dry powder feeder (Scirocco Dry Powder Feeder for Mastersizer 2000); (Malvern Instruments, Inc., Southborough, Mass. 01772) according to the following protocol:

a) Sample Preparation

Prior to measuring particle size, the sample should be well mixed to ensure uniform dispersion. If the sample contains aggregates of any kind, the sample can be mixed to help remove these aggregates; otherwise, the sample should be replaced with a new representative sample that is free of aggregates.

b) Mastersizer 2000 Procedure

1. Turn on the power switch on the Mastersizer 2000 and on the dry powder sample feeder.
2. Allow the laser to warm up for 5 minutes before use.
3. Turn on computer and log on to the workstation. Open the Mastersizer 2000 program. Make sure a green light is displayed on Scirocco 2000 dry powder feeder. The green light indicates that appropriate communication is taking place for use of Scirocco 2000 dry powder feeder.
4. Create a new measurement file and name it using standard lab naming convention or re-open an existing file if adding data to an existing file.
5. Make sure that the dry powder optical is securely locked on the Mastersizer bench. Make sure that the tube connecting the Scirocco 2000 dry powder feeder and the dry powder optical is in place. Tube should not be stretched or kinked.
6. Install the general purpose tray and lock it securely into place inside the dry powder feeder. Confirm that the dust-extraction system is connected and that the proper inlet pressure of at least 80 psi is being received. Verify that all components of the Sirocco 2000 dry powder feeder (feed hopper, sieve basket, etc.) are clean.
7. Adjust the gates on the feed hopper to about 2-3 mm. Weigh and pour 1.5 g of material in sample feeder. Close the cover of the dry powder feeder and lock the latch.
8. Click on "Measure" in the menu bar on the Mastersizer screen. Choose the appropriate SOP file for the sample being analyzed. Fill out any material information as required. Click OK to begin.
9. The instrument will begin its automated calibration before measuring the sample. It will check the zero light level, laser intensity, and align the laser if necessary. It will collect background information and then begin measurement of the sample as specified by the SOP file. [Note: If an obscuration rate of 0.2-20% cannot be achieved, the instrument will time-out or continue to feed sample, but no data will be generated. To resolve this issue, either adjust the gates on the feed hopper to increase sample delivery or narrow the gate to decrease it. Repeat step #8].
10. Once the measurement is complete, a prompt screen will appear asking if a duplicate analysis is desired. Click "NO" and the results will appear on the main screen as a Result Analysis Report.
11. The Dry Powder Feeder must be cleaned between analyses. Remove the feeder tray and vacuum any residue material from the tray. A combination of vacuuming and brushing should be sufficient for proper cleaning.
12. Turn the power off for all equipment when the user is done for the day. Make sure all cleaning procedures are complete.

Example I

Clean-Up of Mono Alkyl Phosphate Surfactant

The efficacy of NUCHAR HD activated carbon particles, commercially supplied by Meadwestvaco, having an average D(v,0.1) value of 5.515, a D (v,0.5) value of 22.096 and a D (v,0.9) value of 65.146 was used to filter mono alkyl phosphate material brandname MAP L-2,3-S, commercially supplied by Rhodia pursuant to the steps outlined below and the results reported in Table II.

First, 500 mL of the unfiltered MAP L-2,3-S mono alkyl phosphate surfactant was added to a 1 liter glass beaker with a stir bar? To the unfiltered surfactant, 2% by wt. of the total volume (10 grams) of the NUCHAR HD particles were added. The surfactant plus carbon mixture was stirred for 16 hours.

The mixture was then filtered through a vacuum filter (0.45 micron pore size, VWR catalog #28199-688). The vacuum filter was pre-washed by passing 250 ml water through the filter, to remove residual PEG on the cellulose acetate, and then the surfactant plus carbon mixture was added to the vacuum filter and the retentate collected as purified surfactant without the carbon particles. (Alternatively, a metal screen, such as a sintered metal laminate filter, with a mesh size smaller than the carbon could have been used to remove the carbon from the surfactant).

The headspace over both the treated and untreated alkyl phosphate sample (MAP 213-S) was collected using Solid Phase Microextraction (SPME). To analyze the headspace, the collected materials were desorbed from the SPME fiber and analyzed using a GC separation with both olfactometry (sniff port) and mass spectrometry detection to obtain both the odor impact and the molecular identity of individual components. The results from both before and after the filtering treatment process are then recorded.

As shown in Table II, the NUCHAR HD removed or reduced the listed contaminants per sniff-port analysis, pursuant to the present invention. The table is representative of one set of conditions. However, by varying conditions such as carbon contact time, number of iterations, carbon quality, etc., the % reduction of each contaminant could be changed and optimized, as needed, for an intended application.

TABLE II

Results of Mono alkyl phosphate treatment

| RT | Peak ID | Mono alkyl phosphate, MAP L-213-S (from Rhodia) untreated (peak area) | Mono alkyl phosphate, MAP L-213-S (from Rhodia) filtered with NUCHAR HD (peak area) | % Reduction vs. unfiltered |
|---|---|---|---|---|
| 18.511 | dodecanal | 60,306,530 | 36,700,274 | 39 |
| 19.758 | dodecanol | 579,815,521 | 346,887,099 | 40 |
| 19.896 | *tbd | 13,920,916 | 10,273,364 | 26 |

TABLE II-continued

Results of Mono alkyl phosphate treatment

| RT | Peak ID | Mono alkyl phosphate, MAP L-213-S (from Rhodia) untreated (peak area) | Mono alkyl phosphate, MAP L-213-S (from Rhodia) filtered with NUCHAR HD (peak area) | % Reduction vs. unfiltered |
|---|---|---|---|---|
| 19.970 | 1-tetradecanol (?) | 8,349,242 | 6,994,922 | 16 |
| 20.041 | tridecanol | 36,915,097 | 17,974,381 | 51 |
| 20.169 | *tbd | 21,520,531 | 12,508,061 | 42 |
| 20.231 | 7,10-dimethyldodecan-6-one | 43,069,022 | 20,091,484 | 53 |
| 20.305 | 3-decanone | 43,971,974 | 18,211,269 | 59 |
| 20.360 | *tbd | 30,056,409 | 16,297,196 | 46 |
| 20.459 | coelution | 34,480,544 | 19,144,762 | 44 |
| 20.670 | *tbd | 21,552,184 | 10,931,376 | 49 |
| 20.861 | cyclotetradecane (?) | 32,536,498 | 17,745,393 | 45 |
| 20.978 | 6-undecanol (?) | 12,408,912 | 0 | 100 |
| 21.029 | *tbd | 14,004,659 | 0 | 100 |
| 21.079 | 4-undecanol | 10,794,448 | 0 | 100 |
| 21.149 | 2-undecyltetrahydropyran | 17,447,462 | 10,026,190 | 43 |
| 21.352 | *tbd | 7,606,308 | 0 | 100 |
| 21.396 | *tbd | 5,236,876 | 0 | 100 |
| 21.579 | 1-hexadecanol (?) | 5,131,170 | 0 | 100 |
| 21.665 | 2-butyltetrahydrofuran | 51,714,666 | 15,671,045 | 70 |
| 21.718 | 7-ethyl-2-methyl-4-undecanol | 13,278,185 | 0 | 100 |
| 21.879 | 3-tetradecanol | 2,495,281 | 0 | 100 |
| 21.990 | dodecyl acetate | 486,533,488 | 119,959,197 | 75 |
| 22.109 | ethylene glycol monododecyl ether | 18,231,228 | 3,057,250 | 83 |
| 22.404 | methyl-6,8-dodecadienyl ether | 43,938,923 | 5,934,187 | 86 |
| 23.409 | coelution | 2,566,659 | 0 | 100 |
| 23.614 | *tbd | 27,803,403 | 7,307,380 | 74 |
| 27.085 | palmitic acid | 18,889,031 | 0 | 100 |

*tbd = compounds where co-elution has prevented a positive identification

Example II

Reduction of Key Volatiles from BC Betaine

The efficacy of NUCHAR HD and Mallinckrodt Activated Charcoal was compared to the efficacy of SA-20 and SA-1500 in the removal of betaine contaminants and the results reported in Table IV, below.

First, 500 mL per beaker of the unfiltered betaine surfactant was added to 4 separate 1 liter glass beakers. To each beaker containing the unfiltered surfactant, 25 grams of the carbon particles (activated charcoal, Nuchar HD, SA-1500, and SA-20) were added individually to a beaker. The surfactant plus carbon mixture was stirred for 16 hours.

The mixture was then filtered through a vacuum filter (0.45 micron pore size, VWR catalog #28199-688). The vacuum filter was washed by passing 250 ml water through the filter, to remove residual PEG on the cellulose acetate, and then the surfactant plus carbon mixture was added to the vacuum filter and the retentate collected as purified surfactant without the carbon particles. (Alternatively, a metal screen, such as a sintered metal laminate filter, with a mesh size smaller than the carbon could have been used to remove the carbon from the surfactant).

The headspace over both the treated and untreated betaine surfactant was collected using Solid Phase Microextraction (SPME). To analyze the headspace, the collected materials were desorbed from the SPME fiber and analyzed using a GC separation with both olfactometry (sniff port) and mass spectrometry detection to obtain both the odor impact and the molecular identity of individual components. The percentage of diphenyl benzene and diphenyl ether removed by each carbon material was then recorded.

As shown in Table IV, the NUCHAR HD and Mallinckrodt Activated Charcoal removed significantly more of the contaminants than the comparative SA-20 and SA-1500 materials.

TABLE IV

Results of Betaine Surfactant Filtration
Reduction of diphenyl benzene and diphenyl ether from betaine surfactant after carbon filtration, as detected by headspace SPME analysis.

| Peak ID | 5% Mallinckrodt Activated Charcoal | 5% SA-20 (Comparative) | 5% NUCHAR-HD | 5% SA-1500 (Comparative) |
|---|---|---|---|---|
| diphenyl benzene | 97.9 | 84.6 | 94.8 | 87.1 |
| diphenyl ether | 97.1 | 56.8 | 85.8 | 78.0 |

Example III

Dentifrice Compositions

Dentifrice compositions made according to the present invention are shown below: These compositions are made using components filtered with the activated carbon materials according to the present invention.

| Ingredient | Ia | Ib | Ic | Id | Ie | If | Ig | Ih | Ii |
|---|---|---|---|---|---|---|---|---|---|
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| G-180 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Sweetener | 0.46 | 0.5 | 0.45 | 0.4 | 0.58 | 0.4 | 0.4 | 0.4 | 0.4 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | 0.50 | | | | | | | |
| NaOH 50% Soln | | | 1.74 | 2.20 | | 2.0 | 2.0 | 2.0 | 2.0 |
| Na Lauryl Sulfate filtered with NUCHAR HD (27.9% soln) | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate, Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Carbon Filtered Surfactant Alkyl Phosphate[1] | | | | | | 3.5 | 6.7 | 3.5 | 3.5 |
| Mallinckrodt Activated Charcoal Filtered Cocamidopropyl Betaine (30% soln) | | | | | | 3.5 | | | |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |

[1]Sodium Laureth Phosphate supplied by Rhodia

Example IV

Mouth Rinse Compositions

Mouth rinse compositions made according to the processes of to the present invention using conventional methods and are shown below with amounts of components in weight %. These compositions are made using components filtered with the activated carbon materials according to the present invention.

| Ingredient | IIIA | IIIB | IIIC |
|---|---|---|---|
| Ethanol, USP 190 proof | 15.000 | 15.000 | 15.000 |
| Glycerin | 7.500 | 7.500 | 7.500 |
| Polysorbate 80, NF | 0.120 | 0.120 | 0.120 |
| Flavor | 0.160 | 0.160 | 0.160 |
| Sweetener Combinations | 0.1 | 0.1 | 0.060 |
| Color Solution | 0.040 | 0.040 | 0.040 |
| Mallinckrodt Activated Charcoal filtered Cetylpyridinium Chloride | 0.045 | 0.045 | 0.045 |
| Benzoic Acid | 0.005 | 0.005 | 0.005 |
| Sodium Benzoate | 0.054 | 0.054 | 0.054 |
| Water | QS | QS | QS |

Example V

Peroxide Mouth Rinse Compositions

Peroxide-containing mouth rinse compositions made according to the processes of to the present invention are shown below with amounts of components in weight %. These compositions are made using components filtered with the activated carbon materials according to the present invention. The mouth rinse compositions provide a pleasant high-impact minty taste during use and noticeable long-lasting fresh breath.

| Ingredient | IVA | IVB | IVC | IVD | IVE | IVF |
|---|---|---|---|---|---|---|
| 35% H$_2$O$_2$ solution | 4.286 | 4.286 | 4.286 | 2.143 | 4.286 | 4.286 |
| Coolant | 0.075 | 0.02 | 0.04 | 0.04 | 0.03 | 0.04 |
| Flavor | 0.145 | 0.135 | 0.135 | 0.15 | 0.135 | 0.135 |
| Poloxamer 407 | 0.75 | 0.75 | 0.750 | 0.10 | 0.10 | 0.10 |
| Glycerin | 11.00 | 11.00 | 11.00 | 20.00 | 20.00 | 20.00 |
| Propylene Glycol | 3.00 | 3.00 | | 4.00 | 4.00 | 4.00 |
| Sweetener Combinations | 0.08 | — | 0.068 | 0.06 | 0.08 | 0.06 |
| Polyphosphate | | | 1.00 | | | |
| NUCHAR HD Filtered Phytic Acid | | 2.00 | | | | |
| Mallinckrodt Activated Charcoal Filtered Cetyl Pyridinium Chloride | | | | 0.074 | 0.10 | 0.10 |
| Na Citrate | 0.212 | 0.212 | | | | |
| Citric Acid | 0.052 | 0.052 | 0.052 | | | |
| Alcohol, USP | | | 5.00 | | | |
| Water, Purified, USP | QS | QS | QS | QS | QS | QS |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing an oral care composition having improved taste, color, odor and/or clarity, wherein said composition comprises a dentifrice component;
   wherein said process comprises the steps of:
   a) providing an unfiltered dentifrice component selected from unfiltered alkyl phosphate surfactants, alkyl phosphate ethoxylated surfactants, lauryl sulfate surfactants, betaine surfactants, antibacterial agents, cetyl pyridinium chloride, metal salts, phytic acids, or mixtures thereof;
   b) filtering the unfiltered dentifrice component with an adsorbent selected from activated carbon having a macro-mesoporous:microporous ratio of at least about 0.9 and a mean particle size of less than 30 microns, to form a filtered dentifrice component; and
   c) incorporating the filtered dentifrice component into the oral care composition.

2. A process according to claim 1 wherein the activated carbon has a macro-mesoporous:microporous ratio of from about 0.9 to about 2.

3. A process according to claim 1 wherein the activated carbon particles are at least partially coated with an active agent to aid in adsorption.

4. A process according to claim 3 wherein the activated carbon has a BET:Total Volume of less than 1600 m^2/g.

5. A process according to claim 1 wherein the unfiltered dentifrice component is an unfiltered surfactant selected from unfiltered alkyl phosphate surfactants, unfiltered alkyl phosphate ethoxylated surfactants, unfiltered lauryl sulfate surfactants, unfiltered betaine surfactants, and mixtures thereof and the filtered dentifrice component corresponds to the filtered version of the selected unfiltered dentifrice component.

6. A process according to claim 5 wherein during the filtering step (b), the unfiltered dentifrice component is in contact with the adsorbent for at least 30 seconds.

7. A process according to claim 5 wherein during the filtering step (b), the adsorbent is mixed with the unfiltered dentifrice component to form a solution and then the adsorbent is removed from the solution to form the filtered dentifrice component.

8. A process according to claim 5 wherein during the filtering step (b), the adsorbent is immobilized into a cartridge and/or column and the unfiltered dentifrice component is then passed through the column and collected to form the filtered dentifrice component.

9. A process according to claim 5 wherein during the filtering step (b), a filter is constructed out of the adsorbent and then the unfiltered dentifrice component is then passed through the filter and collected to form the unfiltered dentifrice component.

10. A process according to claim 1 wherein the adsorbent is selected from activated carbon particles having a particle size a median particle size of less than or equal to about 25 μm.

11. A process according to claim 1 wherein the adsorbent is selected from activated carbon particles having a particle span from about 4 or less.

12. A process according to claim 9, wherein the unfiltered dentifrice component is passed through the filter at a flow rate of from about 0.001 liters/min to about 100 liters/min.

13. A process according to claim 9 wherein the filtered dentifrice component is then recirculated through the adsorbent until the desired amount of contaminant is removed.

14. A process according to claim 1 wherein multiple adsorbents are connected in series.

15. A process according to claim 9 wherein multiple adsorbents are packed in zones within the column and/or cartridge.

16. A method for improving taste, color, odor and/or clarity of an oral care composition, comprising:
a) providing an unfiltered surfactant wherein the unfiltered surfactant is selected from alkyl phosphate surfactants, ethoxylated alkyl phosphate surfactants, and mixtures thereof;
b) filtering the unfiltered surfactant with an adsorbent selected from activated carbon having activated carbon having a mean particle size of less than 30 microns and a macro-mesoporous:microporous ratio of at least about 0.9, to form a filtered surfactant; and
c) incorporating the filtered surfactant into the oral care composition.

17. A method according to claim 16, wherein the activated carbon has a particle span of 4.0 or less.

18. A process for preparing an oral care composition having improved taste, color, odor and/or clarity, wherein said composition comprises a dentifrice component;
wherein said process comprises the steps of:
a) providing an unfiltered dentifrice component selected from unfiltered alkyl phosphate surfactants, alkyl phosphate ethoxylated surfactants, lauryl sulfate surfactants, betaine surfactants, or mixtures thereof;
b) filtering the unfiltered dentifrice component with an adsorbent selected from activated carbon having a BET:Total Volume of less than 1600 m^2/g, a macro-mesoporous:microporous ratio of at least about 0.9 and a mean particle size of less than 30 microns, to form a filtered dentifrice component; and
c) incorporating the filtered dentifrice component into the oral care composition.

* * * * *